United States Patent [19]

Godschalx et al.

[11] Patent Number: 4,774,316

[45] Date of Patent: Sep. 27, 1988

[54] COPOLYMER OF VINYLBENZYL ETHER OF POLYHYDRIC HALOGENATED PHENOLIC COMPOUND AND AROMATIC POLYCYANATE ESTER COMPOUND

[75] Inventors: James P. Godschalx; Edmund P. Woo, both of Midland; Patricia A. Schrader, Coleman; Peter D. Aldrich, Midland, all of Mich.

[73] Assignee: The Dow Chemical Company, Midland, Mich.

[21] Appl. No.: 897,163

[22] Filed: Aug. 15, 1986

[51] Int. Cl.$^4$ ............................................. C08G 63/38
[52] U.S. Cl. .................................. 528/205; 526/289; 526/293; 528/211; 568/645; 568/646; 568/647
[58] Field of Search .............................. 528/205, 211

[56] References Cited

U.S. PATENT DOCUMENTS

| | | | |
|---|---|---|---|
| 3,058,953 | 10/1962 | McMaster | 260/47 |
| 4,116,936 | 9/1978 | Steiner | 526/286 |
| 4,469,859 | 9/1984 | Gaku et al. | 528/159 |
| 4,477,629 | 10/1984 | Hefner, Jr. | 525/113 |
| 4,559,399 | 12/1985 | Hefner, Jr. | 528/120 |
| 4,581,425 | 4/1986 | Hefner, Jr. | 526/72 |
| 4,665,154 | 5/1987 | Varnell et al. | 528/205 |

Primary Examiner—Harold D. Anderson

[57] ABSTRACT

The polyfunctional vinylbenzyl ethers of polyhydric halogenated phenolic compounds are prepared and can be copolymerized with polycyanate ester compounds to provide copolymers having dielectric constants below 3 and a V-O rating in a UL-94 test.

5 Claims, No Drawings

COPOLYMER OF VINYLBENZYL ETHER OF POLYHYDRIC HALOGENATED PHENOLIC COMPOUND AND AROMATIC POLYCYANATE ESTER COMPOUND

BACKGROUND OF THE INVENTION

This invention relates to monomers, polymers and copolymers of vinylbenzyl ethers of polyhydric halogenated phenolic compounds.

Vinyl-terminated compounds are useful in preparing a variety of both thermoset and thermoplastic resins. Additionally, such compounds are useful comonomers in a variety of resin systems. The vinyl moieties are useful polymerization sites in free-radical induced and thermal-initiated polymerization reactions.

Aromatic nuclei are desirably included in the backbone of thermoset and thermoplastic resins because they provide both chemical and structural stability. Other useful moieties included in the backbones of such resins are halogens, such as bromine. The halogens are known to promote fire-resistance to compounds containing them.

In the U.S. Pat. No. 3,058,953, polymers and methods of preparing vinylbenzyl phenol ethers are disclosed. However, the monomers are monofunctional (i.e., they have only one vinyl moiety). In U.S. Pat. No. 4,116,936, polymers of polyvinylbenzyl ethers of polyphenols are disclosed. However, the compounds which are halogenated require a glycidyl bridging group between aromatic rings. In U.S. Pat. No. 4,180,680, methods for preparing halophenolvinylbenzyl ethers are disclosed. Unfortunately, the monomers are monofunctional.

An especially desirable family of thermoset resins is disclosed in U.S. Pat. No. 4,528,366. These resins are aromatic polycyanate resins which can exhibit a dielectric constant of below 3 at 10 kHz. Therefore, these resins are desirably employed in preparing laminates for electronic circuit boards. Such polycyanates have been copolymerized with ethylenically unsaturated monomers in U.S. Pat. Nos. 4,559,425 and 4,559,399. Other polycyanates have been copolymerized with maleimides and ethylenically unsaturated monomers, as described in U.S. Pat. Nos. 4,371,689; 4,393,195; 4,396,745; and 4,469,859. Unfortunately, such compositions require expensive and complicated processing steps and fail to provide a polycyanate resin which exhibits the desired degree of fire retardancy.

In U.S. Pat. No. 4,094,861, a non-inflammable polytriazene is disclosed. Unfortunately, such compounds do not exhibit as desirable physical properties of triazenes prepared with other polycyanates.

It would be desirable to have polyfunctional vinylbenzyl ethers of polyhydric halogenated phenolic compounds. It would further be desirable if such compounds could be copolymerized with other monomers, especially poly(arylcyanate) ester resins to impart fire-resistance to the cured compositions.

SUMMARY OF THE INVENTION

This invention is polyfunctional vinylbenzyl ethers of polyhydric halogenated phenolic compounds comprising a reaction product of a polyhydric halogenated phenolic compound, and an amount of vinylbenzyl chloride sufficient to provide at least 2 vinylbenzyl ether moieties per phenolic compound.

The compounds of this invention can be represented by the formula

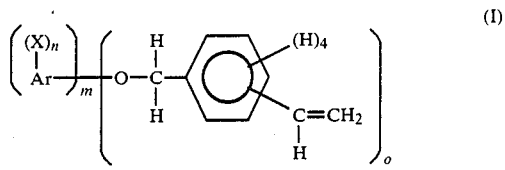

wherein

Ar is an aromatic nucleus of from 6 to 24 carbon atoms;
X is a halogen moiety;
n is an integer of at least 1;
m is an integer of at least 1; and
o is an integer of at least 2.

Another aspect of this invention is a process for preparing polyfunctional vinylbenzyl ethers of polyhydric halogenated phenolic compounds corresponding to the above formula. The process comprises contacting, under suitable reaction conditions, a polyhydric halogenated phenolic compound containing at least 2 hydroxyl moieties with an amount of vinylbenzyl chloride sufficient to provide a reaction product having at least 2 vinylbenzyl ether moieties per phenolic compound.

In yet another aspect, this invention is a copolymer composition comprising a reaction product of the polyfunctional vinylbenzyl ether of the polyhydric halogenated phenolic compounds corresponding to the above formula, and an ethylenically polymerizable comonomer.

In still yet another aspect, this invention is a copolymer composition comprising a reaction product of the polyfunctional vinylbenzyl ether of the polyhydric halogenated phenolic compound

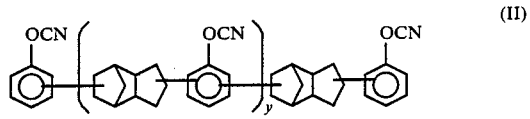

wherein y is greater than or equal to 0.

This invention provides polyfunctional vinylbenzyl ether compounds which are halogenated, and copolymers of such compounds. The vinylbenzyl ethers are useful for promoting certain properties in resins, such as fire-resistance. The copolymers of the vinylbenzyl ethers and aromatic polycyanate ester compounds are useful in fabricating laminates useful for preparing electronic circuit boards. The neat resin employed in preparing the laminates exhibits a dielectric constant below 3, and a V-O rating in the UL-94 test.

DETAILED DESCRIPTION OF THE INVENTION

The polyhydric halogenated phenolic compounds useful in this invention are comprised of an aromatic nucleus substituted with at least 2 hydroxyl moieties (i.e., a polyhydric compound) and a halogen moiety. The aromatic nucleus contains from 6 to 24 carbons. The aromatic nucleus can be a single aromatic ring or multiple aromatic rings which are fused together, or are connected by a direct bond or a hydrocarbon bridging moiety. In addition to being substituted with the halogen and the hydroxyl moieties, the aromatic moieties can be substituted with a variety of substituents provided such substituents do not interfere with the etherification reaction or detract from the physical properties of the polymers or the copolymers. Examples of suitable moieties include alkyl moieties which are of a non-plasticizing length. Typically, alkyl chains of from 1 to 6 carbon atoms do not contribute a plasticizing effect and are suitable. Preferably, the aromatic nucleus is comprised of two aromatic rings connected by a direct bond or an alkyl group.

Additionally, the aromatic nucleus is substituted with a halogen moiety. Preferred halogens are chlorine and bromine, with bromine being most preferred. Enough of the halogen is contained in the aromatic nucleus to provide the desired degree of fire retardancy to a copolymer composition containing the compounds of this invention. Typically, if the aromatic nucleus has a low halogen content, more of the comonomer will be required to provide the degree of fire retardancy. Contrariwise, if the aromatic nucleus contains a high halogen content less of the comonomers need to be employed. Preferably, such halogen amount provides a halogen content of at least 5 weight percent in the cured copolymer composition. Preferably, the aromatic nucleus is a polyhalogenated aromatic nucleus (i.e., contains more than one halogen moiety). Preferably, when the aromatic nucleus contains 2 bromine moieties per aromatic moiety, the bromine moieties are in a meta position on the aromatic moiety because the meta substituted bromines tend to provide a more stable compound.

The polyhydric halogenated phenolic compound can correspond to the formula:

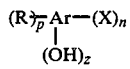   (III)

wherein

Ar, X, and n are as defined in Formula I;

R is hydrogen or an alkyl group of from 1 to 6 carbon atoms;

z is an integer of at least 2; and p is the remaining number of sites available on the aromatic nucleus which are not substituted with the halogen or hydroxyl moieties.

Preferred polyhydric halogenated phenolic compounds are polyhalogenated biphenols. An especially preferred biphenol is tetrabromobisphenol A corresponding to the formula:

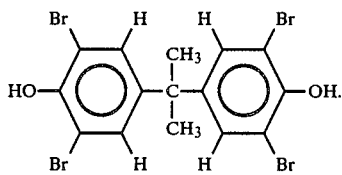   (IV)

Other preferred halogenated biphenol compounds include tetramethyl, tetrabromodihydroxy biphenyl which corresponds to the formula:

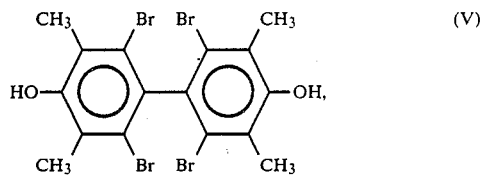   (V)

and 1,2-bis(2,6-dibromo-3,5-dimethyl-4-hydroxyphenyl)ethane which corresponds to the formula

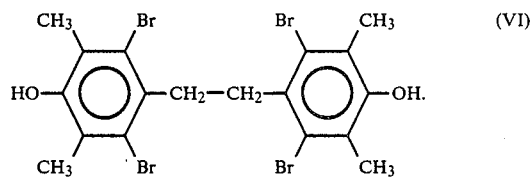   (VI)

These compounds can be prepared by contacting bromine and the respective poly(alkyl)polyhydroxy aromatic compound in the presence of a suitable brominating medium, such as using a Friedel-Crafts catalyst.

Still yet other preferred phenolic compounds are alkylated halogenated mesitols which correspond to the formula

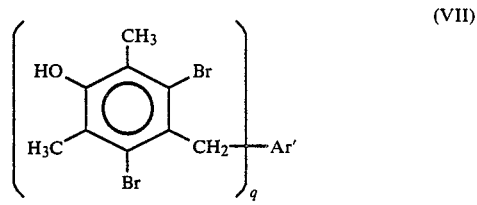   (VII)

wherein Ar' is an aromatic nucleus of $C_6$–$C_{24}$ carbon atoms which can be the same or different as Ar of Formula I and q is an integer of at least 2. A suitable method for preparing such a compound is a Friedel-Crafts alkylation wherein tribromomesitol is contacted with the desired aromatic compound in the presence of a suitable catalyst. Examples of such catalysts are Lewis and Bronsted acids such as $AlCl_3$, $AlBr_3$, and $FeCl_3$. Other suitable reaction conditions are temperatures ranging from about 20° to about 150° C., with higher temperatures producing a quicker reaction. The reaction is conducted at ambient pressures for any suitable time, which typically can range from about 10 minutes to about 14 hours. An inert diluent to solubilize the tribromomesitol can be employed. Haloalkanes such as dichloromethane can be employed. Tribromomesitol can be prepared according to the methods described in K. Auweis and F. Rapp, *Ann.*, 302, 153–71 (1898); O. Jacobsen, *Ann.*, 195, 265–92 (1879); and K. Fries and E. Brandes, *Ann.*, 542, 48–77 (1939).

Preferred polyhydric halogenated phenolic compounds are disclosed in and prepared by the methods described in U.S. patent application Ser. No. 773,685, which was allowed on July 31, 1986, herein incorporated by reference.

Vinylbenzyl chloride is readily available from The Dow Chemical Company and can be prepared according to known methods. Suitable methods are disclosed in U.S. Pat. Nos. 2,780,064; 2,981,758; 3,311,602; Czechoslovakian Pat. No. 83,721; British Pat. No. 792,859; and Russian Pat. No. 318,560.

The polyfunctional vinylbenzyl ethers of the polyhydric halogenated phenolic compounds of this invention are prepared by contacting the polyhydric halogenated phenolic compounds with an amount of vinylbenzyl chloride sufficient to provide at least 2 vinylbenzyl ether moieties per phenolic compound. By "polyfunctional vinylbenzyl ethers" is meant that at least 2 vinylbenzyl ether moieties are provided per compound. The amount of vinylbenzyl chloride can be as much as one, and preferably is an excess of one vinylbenzyl chloride equivalent per hydroxyl equivalent in the phenolic compound. It is most advantageous to cap all the hydroxyls with vinylbenzyl groups because residual hydroxyl groups can detract from the polymer's and copolymer's properties. Preferably, the compounds of this invention are the reaction products (i.e., the isomeric mixture) of contacting only the vinylbenzyl chloride and 1 or more polyhydric halogenated phenolic compounds.

In one method, the polyhydric halogenated phenolic compound can be mixed with a solvent. An amount of base, for example potassium hydroxide, or sodium hydroxide, sufficient to initiate the reaction is added, and the mixture can then be heated. Finally, the desired amount of vinylbenzyl chloride is added, and the reaction product is recovered after cooling.

The vinylbenzyl ether compounds of this invention can be subjected to suitable polymerization conditions to provide polymeric compositions. Such suitable polymerization conditions include polymerizing in the presence of a suitable free-radical catalyst, or treating at suitable polymerization temperatures. Conventional vinyl polymerization reactions are suitable.

The polyfunctional vinylbenzyl ethers of this invention can be copolymerized with other comonomers. Preferred comonomers include monomers which undergo ethylenically unsaturated polymerization reactions. For example, such comonomers include styrene, acrylates and acrylic acids, ethylenically unsaturated hydrocarbons, maleimide compounds and the like. Other comonomers include the epoxy resins and the vinyl ester analogs of the epoxy resins.

A preferred comonomer useful in copolymerizing with the polyfunctional vinylbenzyl ethers of this invention are the aromatic polycyanate ester compounds described in U.S. Pat. No. 4,528,366, herein incorporated by reference. An especially preferred aromatic polycyanate ester is the polyphenol cyanate ester bridged by a dicyclopentadiene moiety which corresponds to the formula

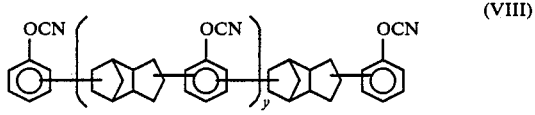

(VIII)

wherein y is a real number of between about zero and 5, inclusive. Preferably, y is a real number of between about zero and 2, inclusive. More preferably, y is a real number of between about zero and 1, inclusive. The most preferred aromatic polycanate ester is depicted when y is 0.2.

The aromatic polycyanate esters of this invention usually exist as a mixture of many isomers. Usually the number given for y in a particular mixture is an average number.

The copolymers of the aromatic polycyanate ester and polyfunctional vinylbenzyl ether of this invention are prepared by melting the comonomers together and heating in the presence of a suitable trimerization catalyst. Examples of suitable catalysts are the cobalt salts. Especially preferred cobalt salts are cobalt naphthenate and cobalt acetylacetonate (CoAcAc).

The amount of the comonomers employed in preparing the copolymer can vary according to the types of properties desired in the copolymer. Increasing the amount of vinylbenzyl ether copolymer can increase the degree of fire resistance, but can be restricted by economical considerations. Typically, at least 8 weight percent, preferably at least 10 weight percent of the vinylbenzyl ether comonomer is employed. An especially preferred copolymer contains 12.2 weight percent of vinylbenzyl ether. Such a cured neat copolymer can exhibit a dielectric constant of below 3 at 10 kHz and V-O rating in a UL-94 test.

Laminates can be prepared by copolymerizing the aromatic polycyanate ester and the polyfunctional vinylbenzyl ether of this invention in the presence of suitable fillers. Examples of such fillers are organic and inorganic fibers and powders, such as glass fibers, Kevlar ®fibers, and ceramic powders. The laminates are useful in preparing electronic circuit boards. The laminates prepared from the copolymers can exhibit a synergistic dielectric constant because the dielectric constant of the neat cured copolymerization product is lower than the dielectric constants of either of the cured homopolymers. Additionally, due to the presence of the bromine of the vinylbenzyl ether component, the laminates can provide a V-O rating in the UL-94 test.

The following examples are provided to illustrate the invention, and do not limit the scope thereof.

Examples

EXAMPLE 1

The Preparation of Vinylbenzyl Ether of Tetrabromobisphenol A

A 1-liter 3-necked round bottom flask is fitted with a reflux condensor, a dropping funnel, and a mechanical stirrer. To this flask is added 12.85 g (0.32 moles) of sodium hydroxide and 400 ml of methanol. The mixture is stirred until the solid has dissolved. Tetrabromobisphenol A (87.34 g, 0.16 moles) is added to the flask and the material heated to 55° C. Vinylbenzyl chloride (54.10 g, 0.35 moles) is added dropwise over a period of 20 minutes. The mixture is maintained at 55° C. for 400 minutes. The mixture is cooled and filtered to remove the solid which is a mixture of the reaction product and sodium chloride. The solid is slurried in 1,400 ml of a 1:1 mixture of methanol and water for 50 minutes and then filtered. The solid is rinsed with water and methanol and then dried in vacuo at 40° C. to give 107 g of a white solid (86 percent yield). The product has a bromine content of about 41 weight percent.

EXAMPLE 2

Copolymerizing the Vinylbenzyl Ether of Tetrabromobisphenol A with Polycyanate Esters An amount of the polycyanate ester of dicyclopentadiene is warmed to 100° C. and poured into beakers. Different amounts of the vinylbenzyl ether of tetrabromobisphenol A are added and the mixture is stirred while heating to 90° C. A 1 percent, based on weight of cobalt, solution of cobalt acetylacetonate in acetonitrile (100 parts per million cobalt) is added and the mixture is stirred well at 90° C. The mixture is degassed in a vacuum at 150° C. for 10 minutes using carborundom boiling stones to aid in degassing. The material is poured into stainless steel parallel plate molds which are preheated to 125° C. The material is cured at 125° C. for 1 hour, 175° C. for 1 hour, 225° C. for 1 hour and 250° C. for 1 hour. The molds are allowed to cool slowly to 100° C. and the plaques are removed.

Six samples of the copolymer composition having different amounts of the vinylbenzyl ether and aromatic polycyanate are prepared, and the degrees of fire resistance are measured according to the UL-94 test. The results are provided at Table I.

TABLE I

| Sample | VBE[1] Content (Percent) | Br[2] Content (Percent) | Burn Time | UL-94 Rating |
|---|---|---|---|---|
| 1 | 24.3 | 10 | 0 | V-0 |
| 2 | 18.2 | 7.5 | 0 | V-0 |
| 3[3] | 12.2 | 5 | 23 sec. | V-0 |
| 4 | 9.7 | 4 | 67 sec. | V-1 |
| 5 | 7.3 | 3 | >300 sec. | HB |
| 6 | 4.9 | 2 | >300 sec. | HB |

[1]Weight percent of bis(vinylbenzyl) ether of tetrabromobisphenol A in the copolymer.
[2]Weight percent of bromine in the copolymer.
[3]The dielectric constant of this sample, Sample 3, is 2.75, measured dry at 10 kHz.

What is claimed is:

1. A copolymer composition comprising a reaction product of a polyfunctional vinylbenzyl ether of a polyhydric halogenated phenolic compound and an aromatic polycyanate ester compound of the formula

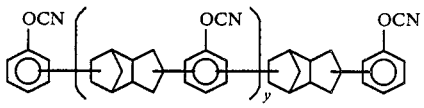

wherein y represents an average value of a real number between about zero and 5, inclusive.

2. The copolymer composition of claim 1, wherein the polyhydric halogenated phenolic compound is tetrabromobisphenol A, and the aromatic polycyanate ester compound is a dicyclopentadiene bridged polycyanate ester which corresponds to the formula

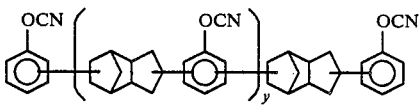

wherein y represents an average value of 0.2.

3. The copolymer composition of claim 2 wherein the copolymer composition exhibits a dielectric constant of less than 3 at 10 kHz, and a V-O rating in a UL-94 test.

4. The copolymer composition of claim 1 wherein y represents an average value of a real number between about zero and 2, inclusive.

5. The copolymer composition of claim 2 wherein y represents an average value of a real number between about zero and 1, inclusive.

* * * * *

UNITED STATES PATENT AND TRADEMARK OFFICE
CERTIFICATE OF CORRECTION

PATENT NO. : 4,774,316

DATED : September 27, 1988

INVENTOR(S) : James P. Godschalx, Edmund P. Woo, Patricia A. Schrader and Peter A. Aldrich It is certified that error appears in the above-identified patent and that said Letters Patent is hereby corrected as shown below:

Column 2, line 37, after "compound" Add -- and an aromatic polycyanate ester compound.
A preferred polycyanate compound is a dicyclopentadiene bridged polycyanate ester which corresponds to the formula--
Column 4, line 66, "2,780,064;" should read --2,780,604--
Column 5, line 60, "polycanate" should read --polycyanate--
Column 6, line 16, "and" should read -- and a--

Signed and Sealed this

Twenty-seventh Day of March, 1990

Attest:

JEFFREY M. SAMUELS

Attesting Officer

Acting Commissioner of Patents and Trademarks